United States Patent [19]
Zabel et al.

[11] Patent Number: 4,504,647
[45] Date of Patent: Mar. 12, 1985

[54] COMPOUNDS HAVING ONE OR MORE ALDIMINE AND OXAZOLIDINE GROUPS, PROCESS FOR THEIR PREPARATION AND THEIR USE AS CURING AGENTS FOR POLYISOCYANATES

[76] Inventors: Lutz D. Zabel, Ruggenstrasse 26, Birmensdorf, Switzerland, 8903; Jürg Widmer, Limmattalstr. 3, Zürich, Switzerland, 8049; Ueli Sulser, Hönggerstrasse 12, Oberengstringen, Switzerland, 8102

[21] Appl. No.: 265,286

[22] Filed: May 20, 1981

[30] Foreign Application Priority Data

May 21, 1980 [DE] Fed. Rep. of Germany ....... 3019356

[51] Int. Cl.$^3$ .................... C07D 263/04; C08G 18/32
[52] U.S. Cl. ........................................ 528/68; 528/73; 548/215
[58] Field of Search ...................... 548/215; 528/68, 73

[56] References Cited
U.S. PATENT DOCUMENTS

| | | | |
|---|---|---|---|
| 3,420,800 | 1/1969 | Haggis | 528/73 |
| 3,567,692 | 3/1971 | Haggis | 528/73 |
| 3,661,923 | 6/1972 | Emmons | 548/215 |
| 3,864,335 | 2/1975 | Emmons | 548/215 |
| 3,912,691 | 10/1975 | Emmons | 548/215 |
| 3,941,753 | 3/1976 | Brinkmann et al. | 528/73 |
| 4,002,607 | 1/1977 | McLeod | 528/73 |
| 4,024,117 | 5/1977 | Emmons | 548/215 |
| 4,032,686 | 6/1977 | Emmons | 548/215 |
| 4,251,637 | 2/1981 | McEntire et al. | 548/215 |

Primary Examiner—Donald G. Daus
Assistant Examiner—S. A. Gibson
Attorney, Agent, or Firm—Abelman, Frayne, Rezac & Schwab

[57] ABSTRACT

New compounds having one, two or three aldimine groups and one, two or three oxazolidine groups in their molecule are curing agents for organic polyisocyanates. Mixtures of said new compounds with polyisocyanates are stable for long periods if humidity is absent, if they however come into contact with water or the humidity of the environment they rapidly cure resulting in elastic or hard polymers. The new compounds are prepared by reacting a diamine or polyamine with up to 6 amino groups with an epoxy compound, yielding a polyamino alcohol, which is thereafter reacted with an aldehyde, e.g. formaldehyde, an aliphatic, cyclic or heterocyclic or aromatic aldehyde.

5 Claims, No Drawings

COMPOUNDS HAVING ONE OR MORE ALDIMINE AND OXAZOLIDINE GROUPS, PROCESS FOR THEIR PREPARATION AND THEIR USE AS CURING AGENTS FOR POLYISOCYANATES

BACKGROUND OF THE INVENTION

This invention is concerned with new compounds having one, two or three aldimine groups and one, two or three oxyazolidine groups. Said new compounds are curing agents for polyisocyanates.

Traditionally polyurea polymers and polyurethane polymers respectively are prepared by mixing polyisocyanates with polyamines and polyhydroxy compounds respectively. If polyamines or polyhydroxy compounds are used as curing agent or component of a curing agent, then the mixtures of polyisocyanates and said curing agents are stable only for very short periods, and they have to be used immediately after mixing.

It is furthermore known that oxazolidines like aldimines and ketimines, i.e. condensation products of keto compounds with amines, generally named Schiff bases, do not react or react only very slowly. Polyaldimines, polyketimines and polyoxazolidines are described in the art and furthermore also their use as components of mixtures with polyisocyanates. With regard to this, reference is made to the British Pat. No. 1 064 841 and the German Offenlegungsschrift No. 2 356 213, No. 1 952 091, No. 1 952 092, No. 2 446 438 and No. 2 458 588. Such mixtures are stable for longer periods if humidity is absent. When they are contacted with water or the humidity of the environment there is liberated by the hydrolysis a polyamine which reacts with the polyisocyanate of the mixture forming urea bonds.

Surprisingly, it now has been found that new compounds having one or more aldimine groups and one or more oxazolidine groups if mixed with polyisocyanates result in mixtures having an extremely long shelf life, provided that the access of humidity is prevented. If however said mixtures are contacted with water, the polymerization proceeds very fast resulting in hard or elastic polymers.

The so cured polymers have a good resistance against chemicals and solvents.

It is thus an object of the present invention to provide new compounds having one or more aldimine groups and one or more oxazolidine groups in their molecule.

A further object of the invention is a process for preparing said new compounds.

Another object of the invention is the use of the new compounds as curing agent for organic polyisocyanates.

A further object of the invention are compositions which are curable by the application of water or humidity of the environment and which contain the new compounds of the invention and furthermore a polyisocyanate.

DETAILED DESCRIPTION OF THE INVENTION

The novel compounds of this invention have one or more aldimine groups and one or more oxazolidine groups in their molecule, i.e. they have the structure of N-[(1,3-oxazolidine-3-yl)-alkylene]alkylidene-imines, and correspond to the following formula I:

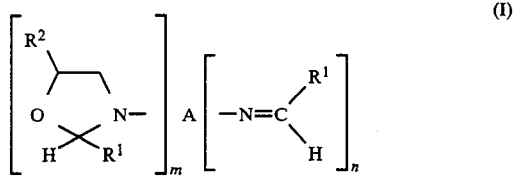

In formula I
m and n are integers in the range of 1 to 3,
$R^1$ is a hydrogen atom, a mononuclear or polynuclear optionally substituted cyclic or heterocyclic radical or an optionally substituted alkyl radical having 1-12 carbon atoms,
$R^2$ is a hydrogen atom, an optionally substituted aryl radical, an aralkyl radical, an alkyl radical having 1-12 carbon atoms, an optionally substituted aryloxymethyl radical, an alkoxymethylradical or an alkenyloxymethyl radical, and
A is an organic radical having the valence m+n, which is an optionally substituted alkyl radical, cycloalkyl radical, aryl radical, aralkyl radical or cycloalkylalkyl radical.

In the compounds of formula I $R^1$ can be a hydrogen atom, a mononuclear or polynuclear aryl radical, e.g. a phenyl radical or a naphthyl radical, a saturated or unsaturated carbocyclic radical, e.g. a cycloalkyl radical or a tetrahydrophenyl radical, a monocyclic or polycyclic heterocyclic radical, e.g. a heteroaryl radical like a furyl radical, an aralkyl radical or an alkyl radical having 1-12 carbon atoms, like e.g. methyl, ethyl, n-propyl, isopropyl, n-butyl, isobutyl, pentyl, hexyl, heptyl, octyl, nonyl, decyl, undecyl, dodecyl or a similar straight chain or branched chain radical.

In the compounds of formula I, furthermore $R^2$ can be a hydrogen atom, an optionally substituted aryl radical, an aralkyl radical, an alkyl radical having 1-12 carbon atoms, like e.g. the corresponding alkyl radicals $R^1$ listed above, an aryloxymethyl radical, like e.g. a phenyloxy or cresyloxymethyl radical, an alkoxymethylradical, like e.g. a n-butyloxymethyl radical or an alkenyloxymethyl radical, like e.g. the allyloxymethyl radical.

If the organic radical having the valence m and n is a substituted alkyl, cycloalkyl, aryl, aralkyl or cycloalkyl radical, the following substituents are preferred: nitro groups, halogen atoms, carboxy groups or thiol groups.

In the compounds of formula I, preferably m is 1 and furthermore also n is 1.

A further object of the present invention is a process for the preparation of the compounds of formula I. In said process a polyamine having the formula II

wherein
A, n and m have the same meaning as in formula I, is reacted with an epoxy compound having the formula III

wherein
$R^2$ has the same meaning as in formula I,
yielding a polyamino alcohol having the formula IV

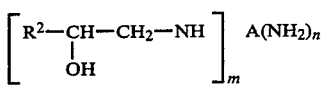

which polyamino alcohol of formula IV is thereafter reacted with an aldehyde having the formula V

wherein $R^1$ has the same meaning as in formula I.

The following reaction scheme illustrates said process:

REACTION SCHEME:

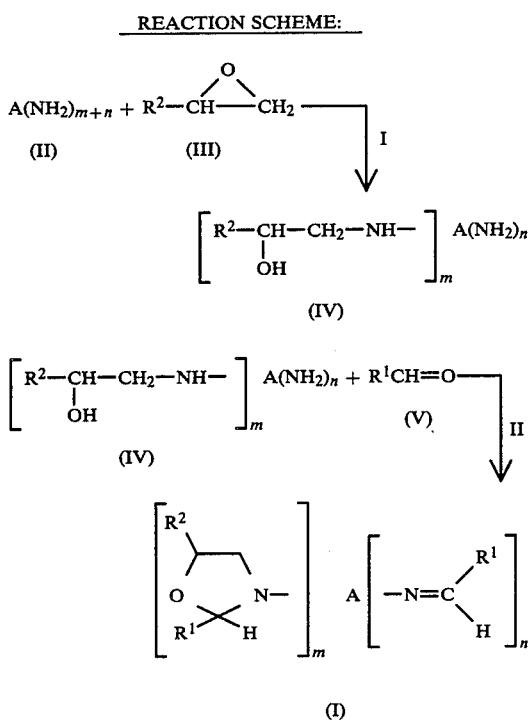

In step I of the inventive process a diamine or polyamine having up to 6 amino groups, which corresponds to formula II is reacted with the epoxide corresponding to formula III. The molar ratio, in which the polyamine and the epoxide are applied preferably is so that always only a simple reaction of the polyamine can occur, i.e. that of the m+n primary amino groups of the polyamine only the amino group m and not the amino group n react with the epoxide group and that furthermore each of the reacting amino groups m reacts only with one epoxide group.

The condensation reaction of step I is generally performed at a temperature in the range of 40°–120° C., optional in a solvent and optionally in the presence of a catalyst. Examples for catalysts which can be used are traces of water, organic carboxylic acids, organic sulfonic acids, inorganic acids or Lewis acids, like e.g. borontrifluoride and zinc chloride.

As outlined above, in preferred compounds of formula I, m and also n is 1, and accordingly the preferred polyamine of formula II used in the first step of the reaction is diamine. Examples for such diamines are diaminoethane, 1,3-diaminopropane, 1,6-diaminohexane, bis-(4-aminocyclohexyl)methane, 2,2-bis-(4-aminocyclohexyl)-propane or 1,4-bis-(3-aminopropoxy)-butane.

Especially preferred however are such polyamines in which one amino group has a higher reactivity than the other amino group or the other amino groups. Examples for such amines are e.g. 3-aminomethyl-3,5,5-trimethylcyclohexylamine, 1,8-p-menthanediamine or 1,6-diamino-2,4,4-trimethylhexane.

The alkylene oxides of formula III, which are reacted with the polyamines of formula II, are preferably alkylene oxides having a lower molecular weight, like e.g. ethylene oxide or propylene oxide. However, also epoxy compounds having a higher molecular weight can be used, like e.g. the following glycidyl-ethers: butylglycidylether, p-cresylglycidylether, phenylglycidylether, allylglycidylether, butanedioldiglycidylether, neopentylglycoldiglycidylether, diglycidethers of 2,2-bis(4-hydroxyphenyl)-propane, the diglycidylethers of ethyleneglycol, the triglycidyl-ether of glycerol, the triglycidyl-ether of trimethylolpropane and further glycidyl-ethers having related structures derived from monohydroxy compounds, dihydroxy compounds or polyhydroxy compounds.

From the reaction of step I of the reaction scheme there result the polyaminoalcohols having the formula IV. Said polyaminoalcohols thereafter are reacted with an aldehyde having the formula V, preferably with an aliphatic, aromatic or heterocyclic aldehyde. During the condensation of the polyaminoalcohol of formula IV with the aldehyde of formula V water is split off, and said reaction water is preferably continuously removed from the reaction mixture, e.g. by using a solvent like cyclohexane, benzene, toluene or chloroform, or optionally by using an excess of the aldehyde and performing an azeotropical destillation.

Examples for aldehydes having the formula V, which can be used in the process for making the inventive compounds of formula I, are the following: aliphatic aldehydes, like formaldehyde, acetaldehyde, propionaldehyde, butyraldehyde and isobutyraldehyde; cyclic aldehydes like tetrahydrobenzaldehyde; heterocyclic aldehydes like furfural; aromatic aldehydes like benzaldehyde and benzaldehydes which are substituted in the o- and/or p-position; and araliphatic aldehydes. Preferred aldehydes used are those having a low boiling range, like e.g. formaldehyde and isobutyraldehyde.

An essential feature of the inventive compounds of formula I is that they have at least one group having the structure:

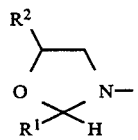

and at least one group having the structure:

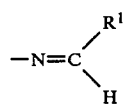

in their molecule.

If said compounds of formula I are brought into contact with water, e.g. the humidity of the environment or atmosphere, then they are hydrolyzed forming polyaminoalcohols having the formula IV. It is known in the art that polyamino compounds react rapidly and completely with polyisocyanates forming polyurea-polyaddition products. The new inventive aldimino-oxazolidine therefore are precursors of curers for organic polyisocyanates.

A further object of the present invention therefore is the use of the inventive compounds of formula I as curing agents for organic polyisocyanates.

A still further object of the present invention are compositions which are curable by the application of water or the humidity of the environment, which comprise an organic polyisocyanate and an aldimino-oxazolidine of formula I.

The compounds of formula I are new compounds and of course also the use as curing component for polyisocyanates and also mixtures of the compounds of formula I with polyisocyanate used for preparing polymeric materials having urea group are not described in the art.

Mixtures of the compounds of formula I and polyisocyanates are stable for long periods if humidity is absent and accordingly have a long shelf life. If they however come into contact with water or humidity, then they cure very fast resulting in elastic or hard polymeric products having a good resistance against chemicals and solvents.

The preferred compounds of formula I used for curing polyisocyanates are those, wherein the group $R^1$, $R^2$, A and the symbols m and n have the preferred meanings outlined above, respectively which result from the preferred amines and epoxy-compounds used in the first step of the synthesis and the preferred aldehydes used in the second step of the synthesis.

Examples for organic polyisocyanates which can be mixed with the inventive aldimino-oxazolidines having the formula I are e.g. aromatic polyisocyanates like 2,4- and 2,6-toluylenediisocyanates, 4,4'-diisocyanato-diphenylmethane and 1,5-naphthylenediisocyanate, and furthermore aliphatic polyisocyanates like e.g. 1-isocyanato-3,3,5-trimethyl-5-isocyanatomethylcyclohexan, 1,6-hexamethylenediisocyanate, trimethylhexamethylenediisocyanate, 1,12-dodecanediisocyanate, 2,6- or 2,4-hexahydrotoluylenediisocyanate, perhydro-2,4' and/or -4,4'-diphenylmethane-diisocyanate and xylylenediisocyanate.

Further examples are 1,6-diisocyanato-2,4,4-trimethyl-hexane and isocyanateprepolymers which are prepared according to processes described in the chemical literature by reacting the above stated polyisocyanates with such compounds which have at least two groups with active hydrogen atoms, which are reactive with isocyanates, and said compounds generally have molecular weights in the range of 200–10,000. Such compounds which are reactive with polyisocyanates are preferably polyhydroxy compounds, especially such having two until eight hydroxy groups per molecule and a molecular weight in the range of 200–10,000. The polyhydroxy compounds which are preferably used as component for making the polyisocyanates in question are diols or triols, or mixtures of diols and triols having an average molecular weight in the range of 200–10,000. Said preferred diol and/or triol components are e.g. polyethers, and the products are produced according to well known processes by an anionic or cationic polymerization of epoxides, like e.g. ethyleneoxide, propyleneoxide, butyleneoxide, styreneoxide or epichlorohydrine.

For preparing the polyisocyanates of the inventive curable compositions however also such polyester-polyols can be used, which are prepared by reacting a polyhydroxy compound, preferably a dihydric and/or trihydric alcohol with a polycarboxylic acid or an anhydride thereof. Examples for polyhydric alcohols are e.g. the isomeric forms of the alkyleneglycol/s and polyalcohols, like e.g. neopentylglycol, cyclohexanedimethanol, glycerol, trimethylolpropane, hexanetriol, diethyleneglycol, triethyleneglycol, tetraethyleneglycol, polyethyleneglycol, dipropyleneglycol, polypropyleneglycol and so on.

Examples for useable polycarboxylic acids and the anhydrides of polycarboxylic acids are the following: succinic acid, adipic acid, sebacic acid, phthalic acid, isophthalic acid, trimellitic acid, pyromellitic acid, the anhydride of phthalic acid, the anhydride of tetrahydrophthalic acid, the anhydride of hexahydrophthalic acid, the anhydride of glutaric acid, the anhydride of maleic acid and the dianhydride of pyromellitic acid.

The curable compositions of the present invention are prepared by mixing the polyisocyanate component with the aldimido-oxazolidine curer of formula I in such amounts that the isocyanate equivalents and the amine equivalents are present in a ratio of 2:2 until 2:1, preferably however in a stoichiometric ratio of 1:1. Accordingly, the curer is present in such amounts or used in such amounts that all the isocyanate radicals present can be reacted with the formed amino groups and hydroxy groups respectively. As outlined above, water and humidity liberates from the inventive compounds substances having free amino groups and hydroxy groups, and it is especially advantageous if only the faster reacting amino groups take part in the curing reaction, because thereby a hydrolysis of isocyanate groups is prevented.

The chemical properties and the physical properties of the cured product can be adjusted to the special field of application, i.e. tailored within broad ranges. If e.g. a polyisocyanate-prepolymer having a low isocyanate content and a high average molecular weight is used, then the cured product will have a good elasticity. If however polyisocyanates having a low molecular weight are used, then the cured products will be hard polymers having a high degree of crosslinkage.

According to a preferred embodiment of the inventive compositions containing the aldimino-oxazolidine of formula I, the polyisocyanate component is a diisocyanate or triisocyanate, having a molecular weight in the range of 150 to 1500.

According to a further preferred embodiment of said compositions the polyisocyanate component is a polyisocyanate prepolymer having a molecular weight in the range of 600 to 80,000.

The inventive compositions can be used for preparing films, foils, coatings, paintings, primers, floor coverings, sealing compositions, impregnating compositions and adhesive compositions. They can be applied to substrates like e.g. wood, concrete, plastic, glass and metal, and e.g. adhesive paste of the inventive composition can be used for glueing other material onto the above stated substrates. Furthermore, the compositions can be also used as binding agent for making sheet materials, like e.g. fibrous sheet materials.

The following examples shall further illustrate the present invention without limiting in any way the scope of protection.

EXAMPLE 1

104 g (1 mol) of aminoethylethanolamine were introduced into a three neck flask equipped with a water separator and a stirrer. The aminoethylethanolamine was stirred, and then a mixture of 158 g (2.2 moles) of isobutylaldehyde and 200 g of cyclohexane was slowly added drop by drop, so that the temperature in the flask did not raise above 50° C. After the total amount of the mixture is added the mixture was heated to a temperature of 70°–90° C. until the calculated amount of water had been separated. Then the excess of aldehyde and the solvent were removed by distillation and the residue distilled under reduced pressure. The resulting compounds have the following formula:

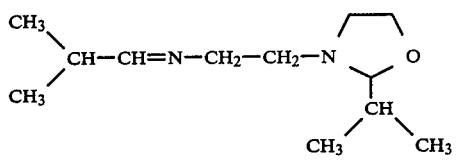

EXAMPLE 2

To 170 g (1 mole) of isophorondiamine were added 12 g of water and said mixture was introduced into a three neck flask equipped with a stirrer, a water separator and a thermometer. Thereafter a solution of 58 g (1 mole) of propylene-oxide and 200 g of cyclohexane were added, and the mixture was left standing for 48 hours. Thereafter, 158 g (2.2 moles) of isobutyraldehyde were added dropwise, so that the temperature did not raise above 50° C. Thereafter, the mixture was refluxed until the calculated amount of water had been separated. The excess of aldehyde and solvent were evaporated. The resulting compound had the following formula:

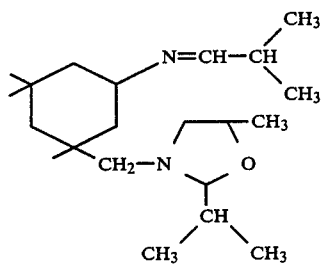

EXAMPLE 3

72 g (1 mole) of 1,3-diaminopropane and 200 g of cyclohexane are introduced into a three neck flask which is equipped with a water separator and a stirrer.

Thereafter, 74 g (1 mole) of butylene-3,4-oxide are added dropwise. Then the reaction mixture is left standing for 24 hours.

Thereafter, 158 g (2,2 moles) of isobutyraldehyde are added drop by drop, so that the reaction temperature does not exceed 50° C. Thereafter, the mixture is refluxed until the calculated amount of water is separated therefrom.

The resulting compound had the following formula:

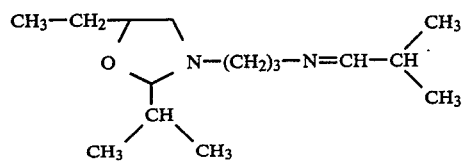

EXAMPLE 4

170 g (1 mole) of isophorondiamine were introduced into a three neck flask and 8 g of water were added. Thereafter 165 g (1 mole) of cresylglycidylether dissolved in 200 ml of cyclohexane were added drop by drop, and attention was paid that the reaction temperature did not raise above 40° C. After all had been added, there is stirred for 1 hour at 40° C., and then the mixture is refluxed for 1 hour.

Thereafter the reaction mixture is cooled to a temperature of 30° and 158 g (2,2 moles) of isobutyraldehyde are added drop by drop, maintaining the reaction mixture at a temperature not exceeding 45° C. After all had been added, the mixture is refluxed until the calculated amount of water had been separated therefrom. Then from the reaction mixture the excess of aldehyde and solvent are evaporated applying a reduced pressure.

The product had the following formula:

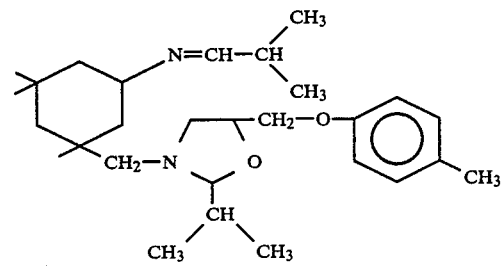

EXAMPLES EXPLAINING THE APPLICATION OF THE PRODUCT

EXAMPLE 5

53 g of the aldimino-oxazolidine prepared according to the process of example 1 were added to 1000 g of an isocyanateprepolymer having a NCO-content of 2%. Said isocyanateprepolymer had been prepared according to a well known process, starting from a bifunctional polypropyleneglycol (having an OH-number of 28) and a propylene-oxide (having an OH-number of 42) which had been started on trimethylolpropane by reacting said hydroxy compounds with 1-isocyanato-3,3,5-trimethyl-5-isocyanatomethyl-cyclohexane.

The mixture of the isocyanate prepolymer and the aldimino-oxazolidine can be stored for several weeks without any remarkable increase of the viscosity of the mixture (see the results stated in the following table). If however the mixture is brought into contact with the humidity of the surrounding air then after 2 hours the surface is no longer tacky.

| Increase of the viscosity when stored at 20° C.: | |
|---|---|
| Lapse of time in weeks | Viscosity in cps |
| 0 | 5000 |
| 1 | 5250 |

-continued

Increase of the viscosity when stored at 20° C.:

| Lapse of time in weeks | Viscosity in cps |
|---|---|
| 4 | 5650 |
| 13 | 6850 |
| 20 | 7900 |
| 27 | 8950 |

EXAMPLE 6

Use as a sealing mass

Into a planetary mixer there were introduced 300 g of dioctylphthalate, 40 g of xylene, 200 g of chalk and 50 g of titanic oxide. Thereafter there were added 150 g of the isocyanate addition product prepared according to the procedure outlined in example 5, and furthermore 50 g of dispersed silica, and the materials were mixed thoroughly. Thereafter, 11.8 g of the curer, prepared according to example 2, were added and the materials were mixed thoroughly. The so resulting sealing mass was degassed and filled into aluminum cartridges.

After a storing time of 3 weeks under normal climatical conditions, the following values were determined:
Breaking elongation of the cured system:
450% at 20 kp/cm²
Formation of a skin at 20° C. and 65% humidity of the air:
90 minutes

EXAMPLE 7

Preparation of a primer 56 g of the aldimino-oxazolidine prepared according to example 4 were added to 100 g of an isocyanate-prepolymer with a NCO-content of 9% and 10 g of desmodur N 75 were added. The isocyanateprepolymer was prepared according to well known processes, by reacting a bifunctional polypropyleneglycol (OH-number=220) with 1-isocyanato-3,3,5-trimethyl-5-isocyanatomethylcyclohexane. The mixture was diluted with 166 g of a mixture of ethylacetate+xylene having a weight ratio of 3:1, and after the addition of the solvent mixture it was mixed vigorously.

| Properties of the resulting product: | |
|---|---|
| The time until the applied coating was dry, so that dust will not cling at a temperature of 20° C. was | 30–40 minutes (depending from the aeration) |
| The Konig pendulum hardness (pendulum-impact) was | 125 |
| The thickness of the applied coating was | 35μ |

EXAMPLE 8

Preparation of a coating

To 100 g of the isocyanateprepolymer prepared according to the process described in example 7, there were added 50 g titanic oxide and 50 g butylacetate and the materials were mixed well. Thereafter, 32 g of the curer prepared according to example 2 were added and it was mixed again well.

A coating of said material was applied to a steel plate and brought into contact with the humidity of the surrounding air.

The coating had the following properties:

| Time until dust did no longer cling was | 2 hours |
|---|---|
| The Konig pendulum hardness was | 120 |
| The thickness of the applied coating was | 70μ |

What is claimed is:

1. A compound having one aldimine group and one oxazolidine group in its molecule, of the formula I:

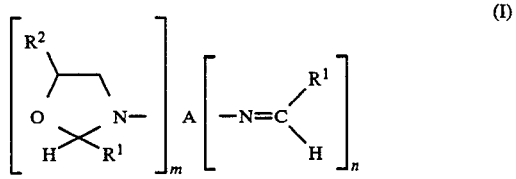

wherein
m and n are integers and are each 1,
R¹ is an isopropyl radical,
R² is a hydrogen atom, an alkyl radical having 1 to 3 carbon atoms, or cresyloxymethyl radical, and
A is a bivalent organic radical selected from the group consisting of —CH₂—CH₂—, —CH₂—CH₂—CH₂—, —(CH₂)₆—,

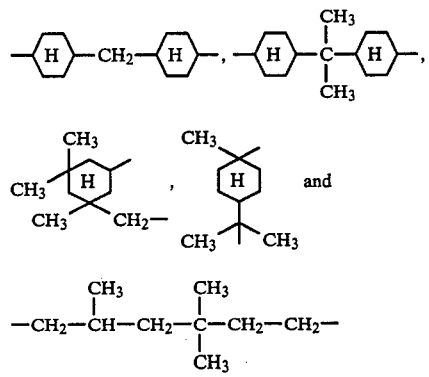

2. Compounds according to claim 1, wherein m is 1 and n is 1.

3. A moisture curable composition which comprises an organic polyisocyanate, and a compound having one or more aldimine groups and one or more oxazolidine groups in its molecule, of the formula I:

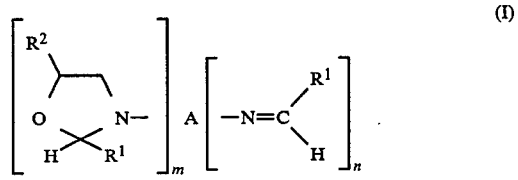

wherein
m and n are integers and are each 1,
R¹ is an isopropyl radical,
R² is a hydrogen atom, an alkyl radical having 1 to 3 carbon atoms, or a cresyloxymethyl radical, and
A is a bivalent organic radical selected from the group consisting of —CH₂—CH₂—, —CH₂—CH₂—CH₂—, —(CH₂)₆—,

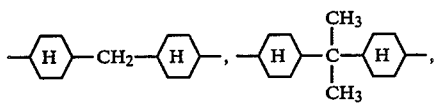

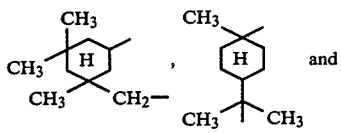

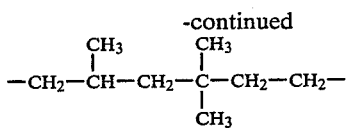

-continued $$-CH_2-\underset{\underset{\phantom{C}}{|}}{CH}-CH_2-\underset{\underset{CH_3}{|}}{\overset{\overset{CH_3}{|}}{C}}-CH_2-CH_2-$$
$$\phantom{-CH_2-}CH_3$$

and wherein a compound of formula I is present in such amounts that the isocyanate equivalents and the amine equivalents are present in the ratio of 2:1 to 1:1.

4. Composition according to claim 3, wherein the polyisocyanate is a diisocyanate or triisocyanate having a molecular weight in the range of 150–1500.

5. Composition according to claim 3, wherein the polyisocyanate is a polyisocyanateprepolymer having a molecular weight in the range of 600–80,000.

* * * * *

UNITED STATES PATENT AND TRADEMARK OFFICE
CERTIFICATE OF CORRECTION

PATENT NO. : 4,504,647
DATED : March 12, 1985
INVENTOR(S) : ZABEL, Lutz Dieter, WIDMER, Jurg, and SALSER, Ueli It is certified that error appears in the above-identified patent and that said Letters Patent is hereby corrected as shown below:

On the title page;

[73] Assignee: Sika AG, vorm. Kaspar Winkler & Co., Zurich, Switzerland

Signed and Sealed this

Thirtieth Day of July 1985

[SEAL]

*Attest:*

DONALD J. QUIGG

*Attesting Officer*     *Acting Commissioner of Patents and Trademarks*